United States Patent [19]

Panneman

[11] 3,972,932
[45] Aug. 3, 1976

[54] NOVEL 2,6-DISUBSTITUTED PHENYL-AMINOGUANIDINE COMPOUNDS

[75] Inventor: Harm Jan Panneman, Titus Brandsmalaan, Netherlands

[73] Assignee: Akzona Incorporated, Asheville, N.C.

[22] Filed: Oct. 24, 1974

[21] Appl. No.: 517,554

[30] Foreign Application Priority Data
Nov. 9, 1973  Netherlands......................... 7315350

[52] U.S. Cl............................ 260/565; 260/343.7; 260/501.14; 260/553 R; 260/558 R; 260/561 R; 424/280; 424/316; 424/320; 424/322; 424/324; 424/326
[51] Int. Cl.²...................................... C07C 133/10
[58] Field of Search............ 260/565, 564 F, 239 A, 260/239 B, 239 E, 293.87, 326.85, 501.14, 343.7

[56] References Cited
UNITED STATES PATENTS
3,804,898   4/1974   Panneman...................... 260/564 F FOREIGN PATENTS OR APPLICATIONS
800,869   9/1958   United Kingdom............. 260/564 F

*Primary Examiner*—Gerald A. Schwartz
*Attorney, Agent, or Firm*—Francis W. Young; Philip M. Pippenger; Hugo E. Weisberger

[57] ABSTRACT

The invention relates to compounds of the general formula:

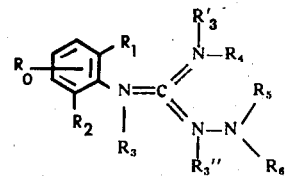

in which one double bond is present between the carbon atom of the guanidine moiety and one of the adjacent nitrogen atoms and $R_0$ stands for hydrogen, halogen, hydroxy, alkoxy or alkyl (1 to 6 C), $R_1$, $R_2$ for halogen, hydroxy, alkyl (1 to 4 C) or alkoxy (1 to 4 C), $R_3$, $R_3'$, $R_3''$ for hydrogen or alkyl (1 to 4 C) on the understanding that one of the substituents $R_3$, $R_3'$ or $R_3''$ is absent because of the presence of the double bond, $R_4$ for hydrogen, alkyl (1-4 C), hydroxy, alkoxy (1-4 C) or amino optionally substituted with one or two alkyl (1 to 4 C) groups, $R_5$, $R_6$ for hydrogen, alkyl (1-6 C), acyl or $R_5 + R_6$ together represent an alkylidene, cyclic alklidene or aralkylidene group, as well as the acid addition salts thereof, provided that, if $R_4$ stands for methyl and $R_0$, $R_3$, $R_3''$, $R_5$ and $R_6$ for hydrogen, $R_1$ and $R_2$ may not represent methyl simultaneously, having a strong and long-acting antihypertensive activity.

4 Claims, 1 Drawing Figure

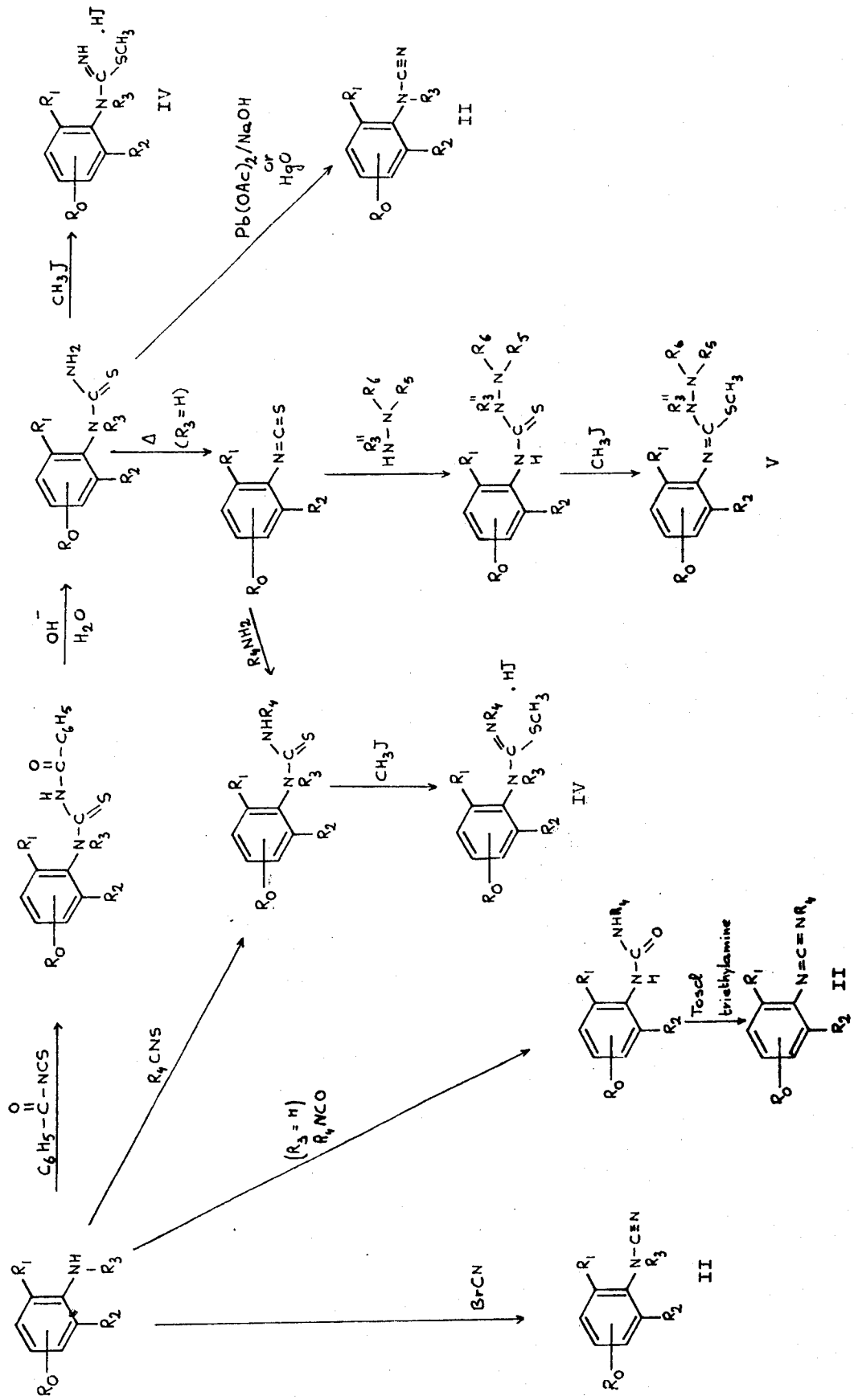

NOVEL 2,6-DISUBSTITUTED PHENYL-AMINOGUANIDINE COMPOUNDS

The invention relates to 1-phenyl-2-aminoguanidine derivatives, the phenyl of which being substituted at the positions 2 and 6, to processes for the preparation of these compounds and to pharmaceutical preparations containing these compounds as the active components.

Surprisingly, it has been found that compounds of the general formula:

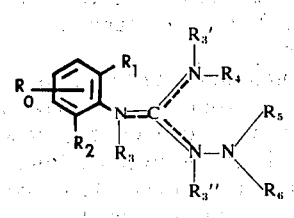

in which one double bond is present between the carbon atom of the guanidine moiety and one of the adjacent nitrogen atoms and $R_0$ stands for hydrogen, halogen, hydroxy, alkoxy or alkyl (1 to 6 C), $R_1, R_2$ for halogen, hydroxy, alkyl (1 to 4 C) or alkoxy (1 to 4 C), $R_3, R_3', R_3''$ for hydrogen or alkyl (1 to 4 C), on the understanding that one of the substituents $R_3$, $R_3'$ or $R_3''$ is absent because of the presence of the double bond, $R_4$ for hydrogen, alkyl (1–4 C), hydroxy, alkoxy (1–4 C) or amino optionally substituted with one or two alkyl (1 to 4 C) groups, $R_5$, $R_6$ for hydrogen, alkyl (1–6 C), acyl or $R_5 + R_6$ together represent an alkylidene, cyclic alkylidene or aralkylidene group, as well as the acid addition salts thereof, provided that, if $R_4$ stands for methyl and $R_0$, $R_3$, $R_3''$, $R_5$ and $R_6$ for hydrogen, $R_1$ and $R_2$ may not represent methyl simultaneously, possess valuable biological activities.

The compounds according to the invention have a strong and long-acting anti-hypertensive activity, even upon oral administration. Unlike many other compounds which produce a blood pressure lowering effect through an adrenergic neuron blocking activity, the present compounds act directly upon the blood pressure regulating centres of the central nervous system without inducing strong sedative side-effects which usually render the use of centrally active anti-hypertensive compounds less desirable.

The compounds according to the general formula I can be prepared by any method commonly used for this type of compounds.

The compounds I may be prepared, for example, by condensation of the cyanamide or the corresponding carbo-diimide of the general formula II:

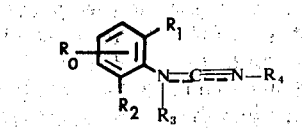

or an acid addition salt thereof, in which $R_0$, $R_1$, $R_2$, $R_3$ and $R_4$ have the meaning mentioned above and in which an extra bond is present between the carbon atom and one of the adjacent nitrogen atoms so that either $R_3$ or $R_4$ is absent, with hydrazine or a hydrazine derivative of the general formula III:

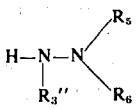

or an acid addition salt thereof, in which $R_3''$, $R_5$ and $R_6$ have the meaning mentioned above.

The compounds I may further be prepared by condensation of an O- or S-alkyliso(thio)urea of the general formula IV:

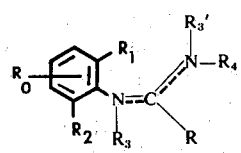

or an acid addition salt thereof, in which $R_0$, $R_1$, $R_2$, $R_3$, $R_3'$ and $R_4$ have the aforesaid meanings and in which an extra bond is present between the carbon atom and one of the adjacent nitrogen atoms, so that either $R_3$ or $R_3'$ is absent, X is oxygen or sulphur and R stands for lower alkyl, preferable methyl or ethyl, with hydrazine or a hydrazine derivative according to the general formula III or an acid addition salt thereof.

The compounds I can moreover be prepared by condensation of a O- or S-alkyliso(thio)-amino urea of the general formula V:

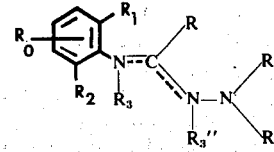

or an acid addition salt thereof, in which $R_0$, $R_1$, $R_2$, $R_3$, $R_3''$, $R_5$, $R_6$, X and R have the aforesaid meanings and in which an extra bond is present between the carbon atom and one of the adjacent nitrogen atoms, so that either $R_3$ or $R_3''$ is absent, with an amine or amine derivative of the general formula VI:

or an acid addition salt thereof, in which $R_3'$ and $R_4$ have the meaning mentioned above.

The latter method is preferably used if it is intended to prepare a compound I in which $R_4$ represents a hydroxy-, alkoxy- or amino-group.

The starting materials required in the aforesaid syntheses, particularly the starting materials of the general formulae II, IV and V are prepared in a way commonly used for this kind of compounds. For the sake of completeness some conventional methods in preparing these starting materials are schematically described in the reaction scheme shown in the accompanying drawings.

The reaction of the starting material II or IV with a hydrazine of formula III or the reaction of the starting material V with an amine or amine derivative of formula VI is preferably performed at a temperature varying between room- and the boiling temperature of the preferably inert solvent used.

Examples of hydrazines according to formula III which may be used in the above mentioned condensation reactions; are for example hydrazine, methylhydrazine, N,N'-dimethylhydrazine, N,N-diethylhydrazine, N-methyl-N'-propylhydrazine, N-methyl-N'-isopropylidenehydrazine, N-ethyl-N',N'-dimethylhydrazine, etc., as well as the acid addition salts thereof.

Examples of amines or amine derivatives that can be used in the condensation reaction with the starting material V are for example ammonia, methylamine, ethylamine, dimethylamine, diethylamine, isopropylamine, isobutylamine, but more particularly hydrazine, methylhydrazine, N,N-dimethylhydrazine, N,N'-dimethylhydrazine, N,N-diethylhydrazine, N-methyl-N'-propylhydrazine, N-methyl-N'-isopropylidene-hydrazine, N-ethyl-N',N'-dimethylhydrazine, hydroxylamine, hydroxylaminemethylether, N-methylhydroxylamine, hydroxylamine-ethylether, hydroxylamine-propylether, N-isopropylhydroxylamine, N-methylhydroxylamine-methylether, etc., as well as the acid addition salts thereof.

In general, the optional substituents at the phenyl ring ($R_0$), at the nitrogen atoms ($R_3$, $R_3'$, $R_3''$, $R_4$, $R_5$, $R_6$) and/or at the oxygen atom ($R_4$ = alkoxy) of the final product I are preferably present already in one of the aforesaid starting products. However, it is also possible to introduce or to modify these substituents in the product obtained after the aforesaid condensation reactions. For example, the N-hydroxy group of a compound I ($R_4$ = OH) can be alkylated in a usual manner with an alkylating agent such as diazomethane, diazoethane or dimethylsulphate or by means of a Williamson synthesis. The nitrogen atom of the 2-amino group of a compound I may be acylated, e.g., with an acylhalide or anhydride, or may be alkylated, e.g., with an alkylhalide or by means of a reduction of the corresponding acyl group in the usual manner. Certain substituents at the phenyl moiety of a compound I can furthermore be converted into another substituent; for example of hydroxyl group can be converted in a conventional manner into an alkoxy group, a methoxy group into a hydroxyl group, etc.

A reaction which is performed preferably after the condensation reaction mentioned above consists of the conversion of a final compound I, in which both $R_5$ and $R_6$ stand for hydrogen, into a compound I, in which $R_5$ and $R_6$ together represent an alkylidene, cyclo alkylidene or aralkylidene group in a conventional manner by reacting a compound I ($R_5$ and $R_6$ = H) with an aliphatic, cyclo-aliphatic or aromatic aldehyde or ketone. In this connection aliphatic aldehydes or ketones with 1–6 carbon atoms as formaldehyde, acetaldehyde, propanal, 2-butanone, 2- or 3-pentanone and, in particular, acetone, the cyclo-aliphatic aldehydes or ketones with 5–12 carbon atoms such as cyclopentanone, cyclohexanone, 4-methyl-cyclohexanone, cyclooctanone, 1-cyclohexyl-3-pentanone or 1-cyclohexylpropanone. and the aromatic aldehydes or ketones with 7 to 12 carbon atoms in which the aromatic group is a phenyl group, such as benzaldehyde, phenyl-acetaldehyde, 1-phenylpropanone or 1-phenyl-3-pentanone, are to be preferred.

Compounds I having an acylated 2-amino moiety ($R_5$ or $R_6$ = acyl) are also preferably prepared by acylating a compound I in which $R_5$ or $R_6$ is hydrogen. The acyl group used is preferably derived from a lower aliphatic or araliphatic carboxylic acid or from a carbamic acid, such as acetic acid, propionic acid, phenyl acetic acid, carbamic acid, N-methylcarbamic acid or N,N-diethylcarbamic acid.

The compounds of formula I are obtained as the free base or as an acid addition salt dependent on the reaction conditions, in which they are prepared. If desired, the free base I can be prepared from the salt I, for example, by reaction with an alkaline compound or by means of an ion-exchanger, and the free base I can be converted into an acid addition salt I in the usual manner.

Pharmaceutically acceptable acid addition salts are obtained by contacting the free base I with organic or inorganic acids such as hydrochloric acid, HBr, HJ, sulphuric acid, phosphoric acid, acetic acid, propionic acid, glycollic acid, maleic acid, fumaric acid, malonic acid, succinic acid, tartaric acid, lactic acid, citric acid, ascorbic acid, salicylic acid, benzoic acid.

The compounds according to the invention can be administered orally as well as parenterally, preferably in a daily dose of fron 0.001 to 50 mg per kg body weight. For this purpose the compounds are incorporated into a suitable dosage form for oral or parenteral administration, for example, a tablet, pill, capsule, solution, suspension, emulsion, in a manner commonly applied for other biologically active compounds.

A dosage form for oral administration is preferred.

Compounds I which are to be preferred in view of their marked antihypertensive activity are those compounds of formula I, in which (whether or not in combination):

— $R_1$ and $R_2$ stand for halogen or alkyl, especially those compounds in which both $R_1$ and $R_2$ represent halogen.
— $R_0$ stands for a substituent selected from halogen or alkoxy at position 4 of the phenyl ring (para position with respect to the guanidino moiety).
— $R_5$ and $R_6$ stand for hydrogen or together for an alkylidene, aralkylidene or cyclo-alkylidene moiety.
— $R_3$, $R_3'$ and $R_3''$ stand for hydrogen.
— $R_4$ represents hydrogen or alkyl.

EXAMPLE I 1-(2,6-dichlorophenyl)-2-aminoguanidine salts 47.4 gram of 1-(2,6-dichlorophenyl)-2-methyl-isothiourea.HJ is suspended in 66 ml of ethanol. To this suspension is added 6.55 ml of hydrazine hydrate after which the mixture is refluxed for 48 hours. The mixture is then cooled down and the precipitate formed is filtered off and recrystallized from ethanol/ether.
Yield: 30.4 g; melting point HJ salt: 208°–210°C.

The HCl salt is obtained by converting the hydroiodide obtained into the free base and treating the free base with a methanolic HCl-solution.
Melting point HCl salt: 280°–283°C.

By treating the free base with maleic acid the corresponding maleate is obtained.
Melting point maleate: 168°–170°C.

EXAMPLE II

In the same manner as described in Example I are prepared by condensation of a hydrazine with 1-(2,6-dichlorophenyl)-2-methyl-isothiourea.HJ:

1-(2,6-dichlorophenyl)-2-methylaminoguanidine.HJ; melting point: 220°–221°C
1-(2,6-dichlorophenyl)-2-dimethylaminoguanidine.HCl; melting point: >280°C
1-(2,6-dichlorophenyl)-2-methyl-2-dimethylaminoguanidine; Rf in methanol:acetic acid (98:2) = 0.55 on $SiO_2$
1-(2,6-dichlorophenyl)-2-isopropylideneaminoguanidine.HCl; melting point: 205°–210°C
1-(2,6-dichlorophenyl)-2-isopropylaminoguanidine.HCl; melting point: 227°–228°C

EXAMPLE III

A.
1-(2,6-dichlorophenyl)-2,3-dimethyl-isothiourea.HCl 13.0 g of 1-(2,6-dichlorophenyl)-2-methylthiourea are dissolved in 115 ml of methanol after which 5.4 ml of methyliodide are added. The mixture is refluxed for 2.5 hours and then cooled down. By adding ether to the mixture a precipitate is obtained that is filtered off.
Yield: 18.9 g; melting point HJ salt: 180°–183°C.
Melting point HCl salt: 173°–175°C.

B.
1-(2,6-dichlorophenyl)-2-amino-3-methyl-guanidine.HCl 12.7 g of the HCl salt obtained in A. are dissolved in 23 ml of methanol after which 2.2 ml of hydrazine.hydrate are added. The mixture is refluxed for 6 days and then evaporated to dryness. With the aid of column chromatography ($SiO_2$, eluted with chloroform:methanol 8:2) the residue is purified and recrystallized from isopropanol/ether.
Yield: 5 g; melting point: 162°–164°C.

C. In the same manner as described in (B). 1-(2,6-dichlorophenyl)-2,3-dimethyl-isothiourea (prepared from (A) by treatment with KOH) is converted with 1,1-dimethylhydrazine, 1,2-dimethylhydrazine and ethylhydrazine respectively into:

1-(2,6-dichlorophenyl)-2-dimethylamino-3-methyl-guanidine (oil);
1-(2,6-dichlorophenyl)-2-methyl-2-methylamino-3-methylguanidine (oil); and
1-(2,6-dichlorophenyl)-2-ethylamino-3-methylguanidine (oil).

Rf in methanol:acetic acid (98:2), 0.70, 0.65 and 0.68 on $SiO_2$ respectively.

EXAMPLE IV 1-(2,6-dimethylphenyl)-2-amino-guanidine.HCl 6.4 g of 1-(2,6-dimethylphenyl)-2-methyl-isothiourea.HJ are dissolved while heating in 10 ml of ethanol to which 1 ml of hydrazine.hydrate has been added. The mixture is refluxed for 18 hours and then cooled.

By adding 20 ml of ether to the mixture a precipitate is formed which is filtered off.
Yield: 5.2 g; melting point HJ salt: 151°–153°C.

This hydroiodide is converted into the corresponding hydrochloride in a conventional manner. Melting point: 192°–193°C.

EXAMPLE V 1-(2-chloro-6-methylphenyl)-2-amino-guanidine.HCl 6.8 g of 1-(2-chloro-6-methylphenyl)-2-methyl-isothiourea.HJ (melting point: 183°–184°C) are suspended in 10 ml of ethanol to which 1 ml of hydrazine.hydrate has been added. The mixture is refluxed for 22 hours and then evaporated to dryness. The residue (oil) is recrystallized from ethanol/ether.
Yield: 5.3 g; melting point HJ salt: 183°–184°C, melting point HCl salt: 239°–241°C.

In a corresponding manner 1-(2-chloro-6-methylphenyl)-2-dimethyl-amino-guanidine is obtained by reaction with 1,1-dimethylhydrazine.

Starting from the hydroiodide of 1-phenyl-2-methyl-isothiourea derivatives with various phenyl substituents the following compounds are prepared in the same manner as described above:

1-(2,6-dichloro-4-iodophenyl)-2-aminoguanidine.HCl; melting point HCl salt: 229°–231°C
1-(2,6-dimethoxy-phenyl)-2-aminoguanidine; melting point HCl salt: 179°–180°C
1-(2-chloro-4,6-dimethoxy-phenyl)-2-aminoguanidine; melting point HCl salt: 193°–194°C
1-(2,6-dihydroxy-phenyl)-2-aminoguanidine
1-(2,6-dichloro-4-hydroxy-phenyl)-2-aminoguanidine.

EXAMPLE VI 1-(2,6-dichlorophenyl)-2-isopropylidene-aminoguanidine.HCl 2.0 g of 1-(2,6-dichloro-phenyl)-2-aminoguanidine.HCl (Example I) are suspended in 4 ml of glacial acetic acid, after which 0.85 ml of acetone is added. The mixture is stirred for 20 hours at room temperature. By adding 10 ml of ether to the mixture a precipitate is obtained that is recrystallized from ethanol/ether.
Yield: 2g; melting point: 208°–210°C.

In a corresponding manner the following compounds are prepared:

1-(2,6-dichlorophenyl)-2-benzylidene-aminoguanidine.HCl; melting point: 216°–217°C
1-(2,6-dichlorophenyl)-2-(2,6-dichlorobenzylidene)aminoguanidine.HCl; melting point: 230°–231°C
1-(2,6-dichlorophenyl)-2-cyclohexylidene-aminoguanidine.HCl; melting point: 140°–155°C
1-(2,6-dichlorophenyl)-2-cyclooctylidene-aminoguanidine.HCl; melting point: 120°–135°C.

EXAMPLE VII 1-(2,6-dimethylphenyl)-1-methyl-2-aminoguanidine.HCl

To 8.2 g of 1-(2,6-dimethylphenyl)-1-methylcyanamide dissolved in 30 ml of ethanol, 3.4 g of hydrazine.hydrochloride are added. The mixture is refluxed for 20 hours followed by evaporation. The residue is recrystallized from ethanol/ether.

Yield: 7.8 g; melting point: 187°–188°C.

By using 1.1-dimethyl-hydrazine instead of hydrazine.hydrochloride 1-(2,6-dimethylphenyl)-1-methyl-2-dimethylaminoguanidine is obtained as an oily substance.

Rf in methanol:acetic acid (98:2) = 0.63 (SiO₂).

In the same manner as described above is prepared the compound 1-(2,6-dichlorophenyl)-1-methyl-2-aminoguanidine.HCl; melting point: 124°–125°C.

EXAMPLE VIII 1-(2,6-dimethylphenyl)-2-amino-2-methylguanidine and 1-(2,6-dimethylphenyl)-2-methyl-aminoguanidine 5.7 g of 2,6-dimethylphenylcyanamide are dissolved in 25 ml of ethanol, after which 3.2 g of methylhydrazine are added. The mixture is refluxed for 20 hours and then evaporated. The remaining oil consists of two isomers. By means of a silica gel column both substances are separated. The compound 1-(2,6-dimethylphenyl)-2-methyl-aminoguanidine (oil) is obtained by elution with chloroform:methanol (8:2); yield: 0.7 g.
Rf in methanol:acetic acid (98:2) = 0.62 on SiO₂ and the compound 1-(2,6-dimethylphenyl)-2-amino-2-methylguanidine (oil) by elution with chloroform:methanol (6:4); yield: 1.8 g.
Rf in methanol:acetic acid (98:2) = 0.54 on SiO₂. The HCl salt of the latter compound melts at 225°–226°C.

EXAMPLE IX

In the same manner as described in Example VII or VIII and starting from 2,6-dimethylphenylcyanamide or 2,6-dichlorophenylcyanamide the following compounds are obtained:

1-(2,6-dichlorophenyl)-2-aminoguanidine.HCl, melting point: 281°C,
1-(2,6-dichlorophenyl)-2-methyl-aminoguanidine.HJ, melting point: 220°–222°C,
1-(2,6-dichlorophenyl)-2-isopropylidene-aminoguanidine.HCl, melting point: 208°–209°C,
1-(2,6-dimethylphenyl)-2-aminoguanidine.HCl, melting point: 192°–193°C.

EXAMPLE X 1-(2,6-dichlorophenyl)-2-amino-3-methyl-guanidine.HCl

To 4 g of N-(2,6-dichloropheyl)-N'-methylcarbodiimide dissolved in 10 ml of absolute ethanol 1.35 g of hydrazine.hydrochloride is added. The mixture is stirred for 20 hours at room temperature and then evaporated to dryness. The residue is recrystallized from ethanol/ether.
Yield: 2.5 g; melting point: 162°–164°C.

In a corresponding manner are prepared the free bases: 1-(2,6-dichlorophenyl)-2-methylamino-3-methylguanidine and 1-(2,6-dichlorophenyl)-2-amino-2,3-dimethylguanidine.

EXAMPLE XI 1-(2,6-dichlorophenyl)-2,3-diamino-guanidine.HCl 10 g of 1-(2,6-dichlorophenyl)-2-methyl-isothiosemicarbazide (oil) obtained from the corresponding HJ-salt (melting point 154°–155°C) by treatment with an equivalent quantity of KOH, are dissolved in 20 ml of ethanol. To this mixture 2.7 g of hydrazine.hydrochloride are added, after which the mixture is refluxed for 20 hours. After cooling the mixture, 50 ml of chloroform are added and stirred for some minutes. The precipitate formed is then filtered off.
Yield after recrystallization from isopropanol: 3 g.
Melting point: 179°–180°C.

EXAMPLE XII 1-(2,6-dichlorophenyl)-2-amino-3-hydroxy-guanidine 6.5 g of 1-(2,6-dichlorophenyl)-2-methylisothiosemicarbazide are dissolved in a mixture of 13 ml of ethanol and 0.9 g of hydroxylamine. The mixture is refluxed for 20 hours. After the evaporation of the mixture the residue obtained is purified by means of column chromatography (SiO₂, elution with chloroform:methanol 8:2).
Yield: 2.5 g (oil); Rf in methanol:acetic acid (98:2) = 0.63 on SiO₂.

EXAMPLE XIII

In the manner as described in Example XI are obtained:
A.  1-(2,6-dichlorophenyl)-2-amino-3-methyl-guanidine.HCl by reaction of 1-(2,6-dichlorophenyl)-2-methylisothiosemicarbazide with methylamine.HCl.
Melting point: 161°–163°C.
B. 1-(2,6-dichlorophenyl)-2-amino-guanidine.HCl by reaction of 1-(2,6-dichlorophenyl)-2-methylisothiosemicarbazide with ammoniumchloride.
Melting point: 280°C.
C. 1-(2,6-dichlorophenyl)-2-methyl-aminoguanidine.HJ by reaction of 1-(2,6-dichlorophenyl)-2(S)-methyl-3-methylaminoisothiourea.HJ with ammoniumiodide.
Melting point: 220°–222°C.
D. 1-(2,6-dimethylphenyl)-1-methyl-2-aminoguanidine.HCl by reaction of 1-(2,6-dimethylphenyl)-1-methyl-2(S)-methyl-3-aminoisothiourea with ammoniumchloride.
Melting point: 186°–188°C.

EXAMPLE XIV 1-(2,6-dichloro-4-tolyl)-2-aminoguanidine.HJ

A. 1-(2,6-dichloro-4-tolyl)-3-benzoylthiourea
To a solution of 10.6 g of 2,6-dichloro-4-toluidine in 80 ml of acetone a freshly prepared solution of benzoylisothiocyanate, obtained from 5.2 g of NH₄CNS + 7.1 ml of benzoylchloride in 120 ml of acetone is added, after which the mixture is refluxed for 1 hour. The mixture is then cooled down and the precipitate formed is removed by filtration. The filtrate is evaporated in vacuo. The residue dissolved in 90 ml of acetone is then poured out into 800 ml of water. A precipitate is formed which is filtered off and recrystallized from 750 ml of methanol.
Yield: 9.75 g; melting point: 184°–185°C.

B. 1-(2,6-dichloro-4-tolyl)-thiourea
9 g of the product obtained in (A) are refluxed for 5 minutes with 113 ml of 2.5 N NaOH. The mixture, cooled down to ambient temperature, is then acidified with 22.5 ml of 36% HCl to pH 4 and then made alkaline with 25% NH₄OH (1.4 ml) to pH 8. The precipitate obtained in this manner is sucked off, washed with water and dried in vacuo.
Yield: 6 g; melting point: 220°–222°C.

C. 1-(2,6-dichloro-4-tolyl)-2-methylisothiourea.HJ 5.9 g of the product obtained in (B) are suspended in 49 ml of methanol, after which 2.5 ml of methyliodide are added. The mixture is then refluxed for 2.5 hours, and after that cooled down and evaporated in vacuo. The residue is titurated after that with 50 ml of ether, dried and recrystallized from ethanol/ether.

Yield: 72. g; melting point: 198°–199°C.

D. 1-(2,6-dichloro-4-tolyl)-2-aminoguanidine.HJ

To 7.18 g of 1-(2,6-dichloro-4-tolyl)-2-methylisothiourea.HJ (C), suspended in 26 ml of ethanol, 1.3 ml of hydrazine.hydrate is added after which the mixture is refluxed for 20 hours. The precipitate formed is filtered off and the filtrate evaporated to dryness. Yield: 6.35 g. Melting point HJ salt: 203°–205°C; melting point HCl salt: 149°–150°C.

EXAMPLE XV 1-(2,6-dichlorophenyl)-2-formylaminoguanidine.HCl 10.4 g of 1-(2,6-dichlorophenyl)-2-aminoguanidine.HCl is suspended into 10 ml of formic acid, after which the mixture is stirred for 20 hours at ambient temperature. A residue that is obtained by adding 50 ml of ether to the mixture is filtered off and dried.

Yield: 10.3 g; melting point: 182°–183°C.

In the conventional manner the following acyl derivatives are obtained:

1-(2,6-dichlorophenyl)-2-acetylaminoguanidine.HCl; melting point HCl: 223°–225°C.
1-(2,6-dichlorophenyl)-2-phenylacetylaminoguanidine
1-(2,6-dimethylphenyl)-2-acetylaminoguanidine.

I claim:

1. A compound selected from the group consisting of a compound of the formula:

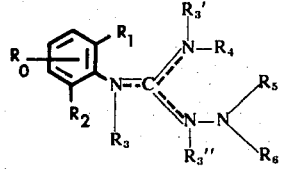

and the pharmaceutically acceptable acid addition salts thereof, in which one double bond is present between the carbon atom of the guanidino moiety and one of the adjacent nitrogen atoms, and in which $R_0$ is selected from the group consisting of hydrogen, halogen, hydroxy, alkoxy containing from 1 to 6 carbon atoms, and alkyl containing from 1 to 6 carbon atoms;

$R_1$ and $R_2$ are selected from the group consisting of halogen, hydroxy, alkyl containing from 1 to 4 carbon atoms, and alkoxy containing from 1 to 4 carbon atoms;

$R_3$, $R_3'$ and $R_3''$ are selected from the group consisting of hydrogen and alkyl containing from 1 to 4 carbon atoms, with the proviso that one of the substituents $R_3$, $R_3'$ or $R_3''$ is absent because of the presence of the double bond;

$R_4$ is selected from the group consisting of hydrogen, alkyl containing from 1 to 4 carbon atoms, hydroxy, alkoxy containing from 1 to 4 carbon atoms, and amino optionally substituted with one or two alkyl groups containing from 1 to 4 carbon atoms;

$R_5$ and $R_6$ together represent an alkylidene group with 1–6 carbon atoms, a cycloalkylidene or cycloalkyl-alkylidene group with 5–12 carbon atoms or a phenylalkylidene group with 7–12 carbon atoms.

2. A compound according to claim 1, in which $R_1$ and $R_2$ are both halogen.

3. A compound according to claim 1, in which the nitrogen atoms of the guanidino moiety ($R_3$, $R_3'$, $R_3''$) are unsubstituted.

4. A compound selected from the group consisting of 1-(2,6-dichlorophenyl)-2-isopropylidene-aminoguanidine and the pharmaceutically acceptable acid addition salts thereof.

* * * * *